(12) United States Patent
Gibert et al.

(10) Patent No.: US 8,147,841 B2
(45) Date of Patent: Apr. 3, 2012

(54) CLOSTRIDIUM TOXIN, AND PROCESS FOR THE PREPARATION OF IMMUNOGENIC COMPOSITION

(75) Inventors: Maryse Gibert, Antony (FR); Michel-Robert Popoff, Clamart (FR)

(73) Assignee: Institut Pasteur, Paris (FR)

( * ) Notice: Subject to any disclaimer, the term of this patent is extended or adjusted under 35 U.S.C. 154(b) by 300 days.

(21) Appl. No.: 11/471,702

(22) Filed: Jun. 21, 2006

(65) Prior Publication Data

US 2011/0223186 A9    Sep. 15, 2011

Related U.S. Application Data

(60) Division of application No. 09/531,438, filed on Mar. 20, 2000, now Pat. No. 7,144,998, which is a continuation of application No. PCT/FR98/01999, filed on Sep. 17, 1998.

(30) Foreign Application Priority Data

Sep. 19, 1997 (FR) ..................................... 97 11710

(51) Int. Cl.
*A61K 39/08* (2006.01)
*C12N 15/63* (2006.01)

(52) U.S. Cl. ................................. 424/190.1; 435/320.1

(58) Field of Classification Search ........................ None
See application file for complete search history.

(56) References Cited

U.S. PATENT DOCUMENTS

| | | | |
|---|---|---|---|
| 4,264,588 A * | 4/1981 | Orcutt ........................ | 424/239.1 |
| 4,292,307 A * | 9/1981 | Zemlyakova .............. | 424/239.1 |
| 5,004,692 A | 4/1991 | Tso et al. | |
| 5,177,017 A | 1/1993 | Lin et al. | |
| 5,192,669 A | 3/1993 | Schoner et al. | |
| 5,266,474 A | 11/1993 | Miller | |
| 5,418,157 A | 5/1995 | Lin et al. | |
| 5,496,725 A | 3/1996 | Yu | |
| 5,529,908 A | 6/1996 | Palva et al. | |
| 5,538,851 A | 7/1996 | Fach et al. | |
| 5,665,363 A * | 9/1997 | Hansen et al. ............. | 424/211.1 |
| 5,874,220 A * | 2/1999 | Fach et al. ................. | 435/6 |
| 5,955,368 A | 9/1999 | Johnson et al. | |
| 6,015,709 A | 1/2000 | Natesan | |

(Continued)

FOREIGN PATENT DOCUMENTS

EP    0 453 216    10/1991

(Continued)

OTHER PUBLICATIONS

Mietzner, Timothy A et al, Infection and Immunity, vol. 60(9), pp. 3947-3951, Sep. 1992, A conjugated Synthetic peptide corresponding to the C-terminal Region of *Clostridium perfringes* Type A Enterotoxin Elicits an Enterotoxin-Neutralizing Antibody Response in Mice.*

(Continued)

*Primary Examiner* — Albert Navarro
*Assistant Examiner* — Ginny Portner
(74) *Attorney, Agent, or Firm* — Oblon, Spivak, McClelland, Maier & Neustadt, L.L.P.

(57) ABSTRACT

The present invention relates to the field of bacterial toxic proteins, in particular toxins from *Clostridium* or other pathogenic organisms using, for example, promoter nucleic acids to control expression of polypeptides such as bacterial toxins.

1 Claim, 9 Drawing Sheets

U.S. PATENT DOCUMENTS

| | | | |
|---|---|---|---|
| 6,133,506 | A | 10/2000 | Topfer et al. |
| 6,280,993 | B1 | 8/2001 | Yamato et al. |
| 6,323,023 | B1 | 11/2001 | Shoseyov et al. |
| 6,403,094 | B1 | 6/2002 | Titball et al. |
| 6,610,300 | B1 * | 8/2003 | Segers et al. ............... 424/184.1 |
| 6,713,617 | B2 | 3/2004 | Minoprio et al. |
| 6,743,430 | B1 * | 6/2004 | Parizek et al. ............. 424/203.1 |
| 6,939,548 | B2 | 9/2005 | Wilkins et al. |
| 7,144,998 | B1 * | 12/2006 | Gibert et al. ................. 536/24.1 |
| 2001/0002256 | A1 * | 5/2001 | David et al. ................ 424/247.1 |
| 2002/0182229 | A1 | 12/2002 | Brown et al. |
| 2008/0089904 | A1 * | 4/2008 | Gibert et al. ............... 424/190.1 |

FOREIGN PATENT DOCUMENTS

| | | | |
|---|---|---|---|
| FR | 2768747 | * | 3/1999 |
| WO | 95/17521 | * | 6/1995 |
| WO | WO 95/17521 | | 6/1995 |
| WO | WO 97/34001 | | 9/1997 |

OTHER PUBLICATIONS

Sirard, Jean-Claude et al, Infection and Immunity, vol. 65(6), pp. 2029-2033, A Recombinant *Bacillus anthracis* Strain producing the *Clostridium perfringens* Ib Component Induces Protection against Iota toxins.*

Gibert, Maryse et al, Gene, vol. 203, (1997) p. 65-73.*

Gibert, M et al, Gene, vol. 203, 1997, pp. 65-73.*

Hunter, et al., "Cloning and Nucleotide Sequencing of the *Clostridium perfringens* Epsilon-Toxin gene and its Pression in *Escherichia Coli* ", Infection and Immunity, vol. 60, No. 1, pp. 102-110, Jan. 1992.

Bullifent, et al., "The Construction of a Reporter System and Use for the Investigation of *Clostridium perfringens* Gene Expression", Fems Microbiology Letters, vol. 131, No. 1, pp. 99-105, Aug. 15, 1995.

Gibert, et al. "BETA2-Toxin, A Novel Toxin Produced by *Clostridium perfringens* ", GEN. pp. 65-73, Dec. 5, 1997.

Hunter, Sec et al, Infection and Immunity, vol. 61(9), pp. 3958-3965, Sep. 1993.

Steinporsdottir, V. et al., FEMS Microbiology Letters, vol. 130, pp. 273-278, 1995.

Hunter, SEC et al, Infection and Immunity, vol. 60(1), pp. 102-110, Jan. 1992.

Garnier, T. et al., Journal of Bacteriology, Sep. 1991, vol. 173(17), pp. 5431-5438.

Kobayashi, T, et al., FEMS Microbiology Letters, vol. 133, pp. 65-69, 1995.

Lyristis, M. et al, Molecular Microbiology, vol. 12(5), pp. 761-777, Jun. 1994.

Narberhaus, F. et al., Journal of Bacteriology, May 1992, vol. 174(10), pp. 3282-3289.

Saint-Joanis, B. et al, Mol. Gen. Genet., 1989, vol. 219, pp. 453-460.

Sauer, Uwe et al., Journal of Bacteriology, vol. 176(21), pp. 6572-6582, Nov. 1994.

Holck, A. et al., Gene, 1990, vol. 91(1), pp. 107-111.

Graves, et al. (1986), The Journal of Biological Chemistry, vol. 261(24), pp. 11409-11415, Aug. 25, 1986.

Brown, Robert Christopher, Ph.D. (1987) Open University (United Kingdom), vol. 58/04C of Dissertation Abstracts International, p. 1203, Development of a Novel Expression System in *Clostridium perfringens* (Gene Expression, Shuttle Vector).

Garnier, T. et al., Plasmid, vol. 19, pp. 151-160, 1988.

Matsushita, C. et al., Microbiology, 1996, vol. 142, pp. 2561-2566.

Melville, Stephen B, et al. Infection and Immunity, vol. 52(12), pp. 5550-5558, Dec. 1994.

Pickett, Carol L. et al., Infection and Immunity, vol. 6496), pp. 2070-2078, Jun. 1996.

Song, Keang-Peng, Ph.D., (1995), Evidence Supporting an Operon Model for the Expression of toxins A and B by *Clostridium difficile* (pseudomembranous colitis, promoter), vol. 56(08-b), Texas Tech. University(Abstract Only).

Brown, Robert Christopher, Ph.D. 1997, Open University, (United Kingdom) Development of a Novel Expression System in *Clostridium perfringens* (Gene Expression, Shuttle Vector), Complete Dissertation, figures and tables, pp. 1-216.

Swiss-Prot Accession No. Q46102, created date Nov. 1996, Cytolethat distending toxin C of *Campylobacter jejuni* .

* cited by examiner

CLOSTRIDIUM TOXIN, AND PROCESS FOR THE PREPARATION OF IMMUNOGENIC COMPOSITION

CROSS-REFERENCE TO RELATED APPLICATIONS

This application is a divisional of U.S. application Ser. No. 09/531,438 filed Mar. 20, 2000, now U.S. Pat. No. 7,144,998, which was a continuation of PCT/FR98/01999 filed Sep. 17, 1998 and claims the benefit of FR 9711710 filed Sep. 19, 1997.

The present invention relates to novel nucleic acids with a transcriptional promoter activity. It also relates to a process for preparing recombinant polypeptides using these nucleic acids, and to recombinant cells containing these nucleic acids. The invention also relates to a novel process for preparing antigens or fragments of antigens, in particular bacterial toxins, more preferably *Clostridium* toxins, for preparing immunogenic and/or vaccine compositions. Still further, it relates to immunogenic and/or vaccine compositions with improved properties.

More particularly, the present invention relates to the field of production of bacterial toxic proteins, in particular toxins from *Clostridium* or other pathogenic organisms. In particular, it relates to the improved production of these toxins, with the aim of producing immunogenic preparations with an increased vaccinating power.

Diseases of bacterial origin (cholera, dysentery, enteritis, etc) are a major cause of death in man and in animals. Such diseases are essentially alimentary in origin, linked to the presence of pathogenic bacteria in ingested elements which colonise the mucosal walls then cause toxicity and tissue necrosis. Pathogenic bacteria come from different genera, particular examples being *Actinomycetes, Bacillus, Bordetella, clamydia, Clostridium, Corynebacterium, Escherichia, Fusobacterium, Listeria, Mycobacterium, Mycoplasma, Salmonella, Staphylococcus, Treponemo* and *Vibro*. Of these pathogenic bacteria, *Clostridium* bacteria form a large class, among which the following species deserve mention: *C. absonum, C. baratii, C. bifermentans, C. chauvei, C. difficile, C. ghonii, C. lituseburense, C. novyi, C. perfringens, C. septicum, C. sordellii, C. subterminale* and *C. tetani*.

The pathogenicity of these pathogenic bacteria has been shown to be linked to their production of toxins or enterotoxins. The large majority of such toxins have now been identified and characterized.

Thus the pathogenicity of strains of *Clostridium septicum*, known to be responsible for atraumatic gangrene, is linked to the expression of a single lethal factor, alpha toxin, the gene of which has been cloned (Ballard et al., Infection and Immunity 63 (1995), 340). The toxin produced by strains of *Clostridium sordellii* has been designated cytotoxin Cs Cyt. Strains of *C. perfringens* are generally classified into 5 types (A-E) depending on the nature of the toxins they produce (alpha, beta, epsilon, iota and enterotoxin). The toxicity of *C. tetani* is linked to the production of a toxin, and *Bordetella* produces pertussis toxin while *C. tetani* produces tetanus toxin. Other toxins will be indicated in the text below.

Currently available treatments are essentially prophylactic in nature. Thus vaccine preparations are produced from cultures of pathogenic bacteria strains. The supernatants containing the toxins are then harvested and undergo different concentration and/or partial purification steps. The supernatants or their filtrates/concentrates then undergo an inactivation step, to produce non virulent toxins, but which retain their immunogenic power (toxoids). Different techniques are available for inactivating toxins, in particular chemical or genetic techniques which will be described below in detail. Further, prior to the inactivation step, supernatants from cultures of different pathogenic organisms are usually combined to obtain cocktails of toxins with the aim of preparing polyvalent vaccines.

Examples of commercially available vaccines are Miloxan®, sold by Rhône-Mérieux (Mérial),France, which protects animals against toxi-infections and enterotoxemia due to strains of *Clostridium perfringens* and *Clostridium sordelli*. More particularly, that vaccine preparation contains toxoids of types B, C and D *Clostridium perfringens*, of *Clostridium septicum*, of *Clostridium novyi*, of *Clostridium tetani*, of *Clostridium chauvei* and of *Clostridium sordellii*. A further example of a polyvalent vaccine is Gletvax5®, sold by Mallinckrodt Veterinary, France, providing protection against collibacilosis in young swine and enteritis from type C *Clostridium perfringens*. More particularly, that vaccine contains *E. coli* antigens, as well as toxoids of the beta toxin of type C *Clostridium perfringens*.

Currently available vaccines, however, have a certain number of disadvantages. They are essentially mixtures of culture supernatants, the composition of which is not precisely defined and for which the reproducibility is thus not entirely assured. Further, the production of polyvalent vaccines protecting against different pathogenic organisms involves separate fermentation of different organisms, meaning that on an industrial scale, culture conditions and safety standards are highly restrictive. Further, the efficiency of some vaccines against certain toxins is limited, in particular those produced in small quantities by pathogenic organisms.

There is thus a genuine need for improving the conditions for preparing, the quality and the efficiency of vaccines against bacterial toxins. The present invention provides an advantageous solution to these problems.

The present invention provides novel nucleic acids enabling expression of transgenes in bacteria, in particular *Clostridium* type bacteria. The invention also provides constructions enabling larger quantities of toxins, in particular for vaccine purposes, to be produced in bacteria, in particular in *Clostridium* type bacteria. In particular, the present invention provides strains of recombinant bacteria, in particular *Clostridium* type bacteria, enabling the amplified production of toxins, either *Clostridium* toxins or toxins from other pathogenic organisms. The invention also provides strains of recombinant bacteria, in particular *Clostridium* type bacteria, enabling a number of toxins to be simultaneously produced.

The invention thus describes a process for producing recombinant toxins enabling the immunogenic character, and thus their protective effect, of vaccine preparations to be increased.

The invention also describes the production of novel toxins by a recombinant route, enabling the range of existing vaccines to be increased, in particular as regards the beta 2 toxin of *Clostridium perfringens* or other toxins which are produced in small quantities by pathogenic organisms, or which are of low immunogenicity.

The invention also provides a considerably easier industrial implementation in that the volumes of supernatants produced and the diversity of the productive organisms used can be significantly reduced.

More particularly, in a first aspect, the invention relates to nucleic acids and genetic constructions for improving the production of proteins in bacteria, in particular bacterial toxins in bacteria of the genus *Clostridium*, in particular *Clostridium perfringens*.

Thus the Applicant has isolated, from the genome of a type C *Clostridium perfringens* strain, the complete gene coding for a toxin, designated beta 2 toxin (SEQ ID no 1). A study of the gene obtained has showed that that gene also comprises, at the 5' end, a transcription promoting region (SEQ ID no 2), which is effective in bacteria in particular in bacteria from the genus *Clostridium*, in particular *Clostridium perfringens*.

More particularly, in its first aspect, the invention provides a nucleic acid characterized in that it has a transcriptional promoter activity and in that it comprises:
(a) all or a portion of sequence SEQ ID NO:3 or a variant thereof; or
(b) a sequence hybridising with all or part of the complementary strand of sequence SEQ ID NO:3.

More preferably, the nucleic acid of the invention comprises all or a portion of sequence SEQ ID NO:3.

Advantageously, the nucleic acid of the invention is constituted by a promoter of the gene for the beta 2 toxin of *Clostridium perfringens* or a fragment thereof.

The term "nucleic acid" as used in the invention means any deoxyribose nucleic acid (DNA) or ribonucleic acid (RNA). More particularly, the DNA can be a complementary DNA (cDNA), a genomic DNA (gDNA) or a synthetic DNA. In the present invention, the term "nucleic acid" is also synonymous with "polynucleotide". The nucleic acids of the invention can be of a variety of origins, in particular bacterial, synthetic or semi-synthetic. They may be isolated using any known molecular biological technique, using structural data and sequences provided in the present application. Thus these nucleic acids can be isolated from libraries using hybridisation techniques. They can also be synthesised chemically or genetically.

The term "portion" or "fragment" of nucleic acid means any nucleic acid comprising at least a portion of the sequence under consideration (for example sequence SEQ ID NO:3) and which retains a transcriptional promoter activity. The sequence portion advantageously contains at least 50 bp, more preferably at least 100 bp. These "portions" can readily be generated using conventional molecular biological techniques, either by enzymatic cleavage and digestion from the fragments described, or by synthesis using nucleic acid synthesisers.

The term "hybridising" as used in the present invention means any hybridisation under normal conditions, which may be stringent or non stringent, as defined below. An example of stringent hybridisation conditions is: Hybridisation at 42° C., 50% formamide, 5×SSC, 1×Denhardt; Wash at 65° C. in 0.1×SSC, 0.1% SDS. Non stringent conditions are: Hybridisation at 37° C., 40% formamide, 5×SSC, 1×Denhardt; Wash at 50° C. in 1×SSC, 0.1% SDS. Stringent conditions are particularly suitable when the nucleic acids are present in small quantities and/or are in purified form. Non stringent conditions are more suitable when the nucleic acid is present in larger quantities and are significantly represented in the sample. Advantageously, "hybridising" sequences are sequences which hybridise under stringent conditions, and which thus have a high degree of structural homology with the sequence under consideration (for example SEQ ID no 2) or its fragments. Further, hybridising sequences can include a region enabling hybridisation and a contiguous region which is not hybridising, but corresponding to flanking regions.

In addition, the transcriptional promoter activity of the "fragments" or "portions" and "hybridising sequences" can readily be determined by the skilled person using the methodology described in the examples. In particular, the activity of the fragments/hybridising sequences can be verified by introducing these nucleic acids to the 5' end of a marker gene, then studying the expression of that marker in a population of cells such as bacteria from the genus *Clostridium*, in particular *Clostridium perfringens*.

The examples below show that the nucleic acids of the invention can significantly amplify the expression of a protein in a bacterium, in particular in a *Clostridium perfringens*.

Thus for a wild strain producing beta 2 toxin, the production level is increased by a factor of about 40 to 80 in the presence of a nucleic acid of the invention. Further, the following examples show that these nucleic acids enable the expression of significant levels of heterologous proteins in bacteria from the genus *Clostridium*. In particular, the examples show that the nucleic acids of the invention can produce heterologous toxins in these bacteria.

In this respect, the invention also concerns a cassette for expression of a transgene, characterized in that it comprises, in the 5'→3' direction:
a nucleic acid as defined above; and
said transgene.

In the cassette of the invention, the nucleic acid and the transgene are operationally connected together (i.e., so that the nucleic acid enables expression of said transgene).

Advantageously, the cassette of the invention further comprises a transcriptional terminator, at the 3' end of the transgene.

Further, the cassette of the invention can also advantageously comprise a secretion signal which can induce or increase secretion of the expression product of the transgene by the cells. Advantageously, this secretion signal is located between the nucleic acid of the invention and the transgene, in the same reading frame as the latter.

To this end, the inventors have also demonstrated the existence in the identified gene of such a secretion signal, which is particularly active in bacteria from the genus *Clostridium*. This signal is represented by residues 268-357 in sequence SEQ ID NO:1, and separately in SEQ ID NO:5. This signal, or any variant or active fragment thereof, constitutes an advantageous embodiment of the invention.

As indicated above, the invention is particularly suitable for the production of toxins or fragments or variants of toxins. Thus in a particular embodiment, the expression cassette of the invention is characterized in that the transgene codes for a toxin or a toxin fragment or variant. More particularly still, the transgene codes for a toxin or a toxin fragment or variant of a pathogenic bacterium.

The term "toxin" as used in the invention means any peptide, polypeptide or protein produced by a pathogenic bacteria, and involved in said pathogenic activity. It may be a factor which is directly responsible for the toxicity of the bacterium, or it may participate in that toxicity. A toxin "fragment" can be constituted by any portion of a toxin, which has retained certain immunogenic features of the toxin. In particular, bacterial toxins have been described as often presenting different distinct functional domains, in particular a domain involved in toxic activity (catalytic site) distinct from other domains involved in site recognition or in interactions with partners. A toxin "fragment" of the invention is advantageously constituted by a domain which is deprived of toxic activity, but which retains an immunogenic power. A toxin variant may, for example, be constituted by a derivative resulting from genetic modifications of the sequence coding for said toxin or toxin fragment. Examples of such genetic modifications are mutations, deletions, fusions, etc. In general, mutations affect 1 to 10 residues, preferably 1 to 5 residues. These mutations are mutations which modify the amino acid coded for, and thus which modify the protein sequence. Deletions can be internal or terminal deletions. They can affect up to 40% of the entire sequence. Fusions consist of introducing supplemental regions at the 5' and/or 3' end of the sequence, or possibly of inserting such regions into the sequence. These modifications can be carried out with the aim either of reducing or of removing the toxicity of these proteins, or of improving their production or stability, for example. Such genetic modifications can be carried out under conventional molecular biological conditions, and are illustrated in the prior art and in the remainder of the text of the present application.

More particularly, the cassettes of the invention are suitable for the production of the following toxins or variants:

The beta 2 toxin of *Clostridium perfringens* or any immunogenic fragment. The hydrophilicity profile of beta 2 toxin is shown in FIG. 8. This profile shows a number of hydrophilic regions, which define particular fragments within the context of the invention. These regions are in particular located at amino acid residues 40-55, 105-120, 160-170, 175-188, 200-210 and 250-260 as shown in SEQ ID NO:2. Further, fragments of the beta 2 toxin which are free of toxicity are trypsic fragments of 24, 15 and 13 kDa described in the examples. Constructions for expressing this toxin are described in the examples.

The beta 1 toxin of *Clostridium perfringens* or any immunogenic fragment. The sequence for this toxin has been described in the literature (Hunter et al., Infect. Immun. 61 (1993), 3958-3965). Constructions for expressing this toxin are described in the examples.

The iota toxins of *Clostridium perfringens* or any immunogenic fragment. The sequence for genes coding for iota 1 toxins (gene 1a) and iota 2 toxins (gene 1b) have been described in the literature (Perelle et al., Infect. Immun. 61 (1993) 5147-5156).

The alpha toxin of *C. novyi* or any immunogenic fragment. The gene sequence for this toxin (tcnα gene) has been described in the literature (Hofmann et al., Mol. Gen. Genet. 247 (1995) 670-679).

The alpha toxin of *C. septicum* or any immunogenic fragment. The gene sequence for this toxin has been described in the literature (Ballard et al., Infect. Immun. 63 (1995) 340-344).

The A and B toxins of *C. difficile* or any immunogenic fragment. The gene sequence for this toxin has been described in the literature, as well as different immunogenic regions (Von Eichel-Streiber et al., Mol. Gen. Genet. 233 (1992) 260-268; Von Eichel-Streiber et al., J. Gen. Microbio. 135 (1989) 55-64; Von Eichel-Streiber et al., J. Bacteriol. 174 (1992) 6707-6710).

The epsilon toxin of *C. perfringens* (Worthington et al., Onderstepoort J. Vet. Res. 40 (4) (1973) 145-152/Hunter et al., Infect. Immun. 60, (1992) 102-110).

The enterotoxin of *C. perfringens* (McClane, Toxicon. 34 (1996) 1335-1343).

The toxin of *C. chauvoei* (Crichton et al., Australian Vet. J. 63 (1986) 68).

The L cytotoxin of *C. sordellii* or any immunogenic fragment. The gene sequence for this toxin has been described in the literature (Green et al., Gene 161 (1995) 57-61), also different immunogenic regions. In particular, this toxin is constituted by a protein of about 270 kDa and different antigenic fragments have been described.

The pertussis toxin.

The tetanus toxin, the botulism toxin, in particular the C fragment of these toxins which is the immunogenic fragment (Makoff et al., Bio/Technology 7 (1989) 1043; Figueiredo et al., Infect. Immun. 63 (1995) 3218-3221; Wells et al., Molecular Microbiol. 8 (1993) 1155-1162; Boucher et al., Infect. Immun. 62 (1994) 449-456; Clare et al., Bio/Technology 9 (1991) 455; Clayton et al., Infect. Immunol. 63 (1995) 2738-2742).

The nucleic acids and/or expression cassettes of the invention can be inserted in a vector which constitutes a further aspect of the present invention. It is advantageously a vector which is functional in bacteria, i.e., capable of penetrating into bacteria and transporting the nucleic acids of the invention thereto. More preferably, such a vector comprises either a functional origin of replication in a bacterium, or sequences enabling it to integrate into the genome of a bacterium. More particularly, it is a plasmid, phage, episome, etc . . . Further, certain vectors may advantageously comprise two origins of replication, one functional in bacteria of the genus *E. coli*, and the other functional in bacteria of the *Clostridium* type, for example.

The vector of the invention is particularly preferably a vector which is functional in bacteria from the genus *Clostridium*, in particular in *Clostridium perfringens* bacteria. As an example, it may be a vector derived from the plasmid pAT19 described by Trieu-Cuot et al. (Gene 102 (1991) 99-104). Such a derivative is, for example, the vector pMRP353 or the vector pMRP268 as shown in FIGS. 2-4.

The invention further concerns any recombinant cell comprising a nucleic acid or an expression cassette or a vector as defined above. The recombinant cell is advantageously a prokaryote cell, preferably a bacterium. Particularly advantageously, the cell of the invention is a bacterium of the genus *Clostridium* selected from *C absonum, C. baratii, C. bifermentans, C. chauvei, C. difficile, C. ghonii, C. lituseburense, C. novyi, C. perfringens, C. septicum, C. sordelli, C. subterminale* and *C. tetani*. More preferably still, it is a *C. perfringens* bacterium.

The recombinant cells of the invention can be prepared using any of the techniques known to the skilled person for introducing a nucleic acid into a cell. It may be a physical technique (electroporation, bombardment, gene gun, etc.), a chemical technique (precipitation with $CaPO_3$, use of chemical transfer agents: cationic lipids, polymers, etc., or other methods such as cell fusion, conjugation, etc. (Scott et al., Gene 82 (1989) 327-333; Phillips-Jones, FEMS Microbiol. Letters 66 (1990) 221-226; Allen et al., FEMS Microbiol. Letters 70 (1990) 217-220).

Further, a recombinant cell of the invention may comprise a plurality of cassettes or vectors of the invention comprising different transgenes, and thus produce either different toxins, or different fragments of the same toxin.

The invention also relates to a process for producing a polypeptide comprising introducing a transgene coding for said polypeptide into a host cell under the control of a promoter as defined in the invention, then recovering said polypeptide.

A particular process for producing polypeptides of the invention comprises culturing a recombinant cell as defined above comprising an expression cassette or a vector, the transgene coding for said polypeptide.

More particularly, in the process of the invention, the cell is a bacterium of the genus *Clostridium*, more preferably *C. perfringens*.

The process of the invention is particularly suitable for the production of a toxin or a toxoid. The term "toxoid" is well known to the skilled person, and designates any inactivated form of a toxin, i.e., deprived of toxic nature, but retaining the immunological properties of the toxin. More preferably, the process of the invention is used to produce a toxin (or a corresponding toxoid) selected from the group comprising the alpha, beta (beta 1 and beta 2), iota (1 and 2), epsilon and enterotoxin of *C. perfringens*, pertussis toxin, tetanus toxin, the alpha toxin of *C. septicum*, the alpha toxin of *C. noyvi*, the A and B toxins of *C. difficile* or the L cytotoxin of *C. sordellii*.

More generally, then, the invention concerns the use of a nucleic acid as defined above for the production of polypeptides.

The invention also concerns a process for preparing an immunogenic composition comprising the following steps:
a) expressing one or more toxins (or the corresponding toxoids) in a cell, as defined above;
b) harvesting the supernatant;
c) optionally, treating the supernatant to purify or concentrate the toxin(s) or toxoid(s);
d) inactivating the toxin(s); and
e) optionally, packaging the inactivated toxin(s) or the toxoid(s).

In the process of the invention, an optional supplementary step carried out before or after step d) comprises grouping the supernatant with other culture supernatant(s) containing a different or identical toxin, or a corresponding toxoid. These other supernatant or supernatants may originate from recombinant strains as defined in the invention, or from any other strain, which may or may not be recombinant, producing the toxin under consideration. In the process of the invention, two supernatants are advantageously combined, which originate from cultures of recombinant bacteria of the invention producing a different toxin.

a) Production of Supernatants

The first step in producing the immunogenic compositions of the invention consists of producing culture supernatants containing the toxin or toxins under consideration. At least a portion of the supernatants advantageously originate from a recombinant bacterial strain comprising a cassette or a vector as defined above. For polyvalent vaccines, a plurality or all of the supernatants can be supernatants from recombinant bacterial strains comprising a cassette or a vector as defined above. More preferably, they are recombinant strains of *Clostridium*, more preferably *C. perfringens*. One advantage of the process of the invention is that it limits the number of different organisms used for fermentation. Further, the recombinant strains used can also comprise a plurality of cassettes or vectors of the invention, such that they simultaneously produce a plurality of toxins. This embodiment advantageously further reduces the number of fermentations in the production process.

The production can be carried out under the culture conditions described above, in fermenters of 50 to 1500 liters. When the supernatants containing the toxins have been produced, they undergo different treatments.

b) Harvesting Supernatants

The supernatants are harvested using conventional biological techniques which are well known to the skilled person. In particular, the supernatants can be recovered by simple filtration to separate the cells.

c) Treatment of Supernatants

In order to improve the quality of the final preparation, the supernatants can optionally undergo supplementary treatments such as filtration, centrifugation, concentration, etc. These treatments clarify the supernatants, and partially purify the toxins. These techniques are known to the skilled person.

Further, in the case of polyvalent vaccines, different supernatants can be collected at this stage.

d) Inactivation of Toxins

In order to prepare an effective immunogen, it is of course important that the antigen used is free of the toxicity of the toxin against which protection is sought. With the aim of generating these inactivated toxins (toxoids), different techniques are possible (Rappuoli et al., Int. Arch. Allergy Immunol. 108 (1995) 327-333).

Chemical inactivation

Chemical toxin inactivation has long been described, and continues to be used for numerous immunogenic preparations. Thus with the aim of inactivating bacterial toxins without affecting their immunogenic properties to too great an extent, the supernatants of the process of the invention can be treated with the following compounds: formol, β-propiolactone, iodine, formaldehyde or glutaraldehyde. More precise conditions and doses which can be used are known to the skilled person, and have been described, for example, by Rappuoli R (In Woodrow G C, Levine M M (eds): New Generation Vaccines, New York, Dekker, 1990 p. 251-268), hereby incorporated by reference.

Physical inactivation

The toxins can also be physically inactivated, for example by irradiation.

High pressure inactivation

High pressure treatment can also be used to effect inactivation.

Genetic inactivation

A further approach to inactivating toxins resides in genetic modification of their primary structure. In this case, the products liberated into the supernatant are already toxoids, and it is not necessary to carry out a supplementary inactivation step. Genetic inactivation (or detoxification) essentially consists of modifying the nucleic acids coding for the toxins, such that one or more amino acids are changed and the protein produced is free of toxicity. As an example, it is possible to replace the amino acids involved in enzymatic activity, and thus toxicity, with different amino acids which do not have this activity. It is also possible to delete regions of the toxin so as to produce non-toxic, immunogenic fragments. This strategy can be carried out when epitopes of the toxins have been identified (for example by epitope scanning) or are identifiable (for example from a hydrophobicity profile). This strategy can also be applied to the production of fragments (for example trypsic fragments) for which the absence of toxicity has been demonstrated. Further, genetic modification can also be carried out by random mutagenesis and selecting clones producing a toxoid. Such a strategy has already been successfully carried out to produce toxoids of the diphtheria toxin by mutagenesis using nitrosoguanidine (NTG) (Giannini et al., Nucleic Acids Res. 12 (1984) 4063-4069). Further, the production of toxoids by site-specific mutagenesis has also been successfully carried out using genes of pertussis and cholera toxins (Pizza et al., Science 246 (1989) 497-500; Pizza et al., J. Exp. Med. 6 (1994) 2147-2153; Fontana et al., Infect. Immun. 63 (1995) 2356-2360).

The toxoids produced are then directly used to prepare vaccine compositions.

e) Formulation

The toxoids are generally packaged using conventional pharmacological techniques in a manner suitable for vaccine use. The toxoids are preferably formulated in the presence of adjuvants or excipients which are suitable for the production of injectable solutions. In particular, injection is advantageously carried out subcutaneously or systemically. The doses of antigen (toxoid) used are generally those which will ensure the best protection without inducing a significant secondary reaction. The conditions and sites for injection, and techniques for determining doses, are illustrated in detail in the pharmacopia (*Vaccinum Clostridii Perfringentis*, Chap. 363).

The invention also relates to any immunogenic preparation comprising a toxin produced in a recombinant strain as defined above. More particularly, the invention relates to any immunogenic preparation comprising a toxoid of recombinant beta 2 toxin, optionally combined with other toxoids.

The present invention will now be described in more detail with the aid of the following examples which should be considered to be illustrative in nature and are in no way limiting.

LIST OF SEQUENCES

Figure 1:
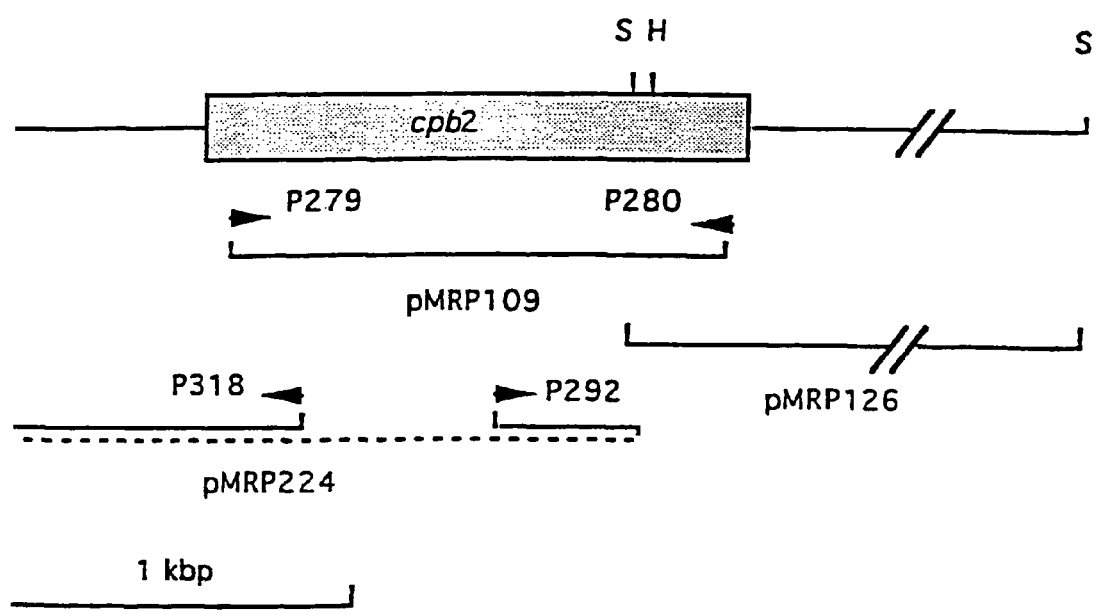
FIG. 1: Cloning strategy for the complete gene for the beta 2 toxin of *C. perfringens*. H: HindIII; S: Sau3A

SEQ ID no 1: Gene sequence for beta 2 toxin of *Clostridium perfringens*.

SEQ ID no 2: Sequence for beta 2 toxin gene promoter of *Clostridium perfringens*.

SEQ ID no 3: Sequence for beta 2 toxin gene promoter of *Clostridium perfringens*.

SEQ ID no 4: Nucleotide sequence for secretion signal of beta 2 toxin gene of *Clostridium perfringens*.

SEQ ID no 5: Protein sequence for secretion signal of beta 2 toxin gene of type C *Clostridium perfringens*.

SEQ ID no 6: Sequence of primer P318.

SEQ ID no 7: Sequence of primer P292.

MATERIALS AND METHODS

1. Bacterial Strains and DNAs Used.

The bacterial strains used are mentioned in Tables 1 and 2. *Clostridium* strains were cultivated in the presence of Trypticase (30 g/liter), yeast extract (20 g/liter), glucose (5 g/liter) and cysteine-HCl (0.5 g/liter), pH 7.2 (TGY medium) at 37° C. under anaerobic conditions.

Total DNA and plasmidic DNA from *Clostridium* were extracted and purified using the technique described by Perelle et al. (Infect. Immun. 61 (1993) 5147-5156).

Plasmids pUC19 and pUC18 (Appligene Strasbourg, France) were used for the cloning experiments in TG1 *E. coli*, and shuttle vectors pAT19 (Trieu-Cuot et al., Gene 102 (1991) 99-104) and pJIR750 (Bannan and Rood, Plasmid 229 (1993) 233-235) were used for cloning and expression experiments in *Clostridium*, in particular in *Clostridium perfringens* 667-76, a negative lecithin strain.

2. The synthetic oligonucleotides and hybridisation experiments were those described by Perelle et al., 1993 (supra).

3. The PCR amplification experiments were carried out in a total volume of 100 µl using 100 ng of DNA as described above (Perelle et al, 1993, supra).

4. Ligations and transformations were carried out using standard molecular biological protocols (Sambrook et al., Molecular Cloning: A Laboratory Manual, Cold spring Harbor Laboratory Press, Cold Spring Harbor, N.Y., 1989).

5. The beta 2 toxin was purified and microsequenced using the protocol described in International patent application WO 95/17521.

6. The cytotoxicity was determined using the following test: intestinal I407 cells (ATCC) were cultivated in modified Dulbecco medium (DMEM) supplemented with 5% of fetal calf serum. The I407 cells were spread onto 96 well culture plates (Falcon, Becton Dickinson) and cultivated for 24 hours at 37° C. in an incubator containing 5% $CO_2$ to obtain monolayers. Series dilutions by a factor of 2 of samples with a final volume of 100 µl were added to the monolayers. The cells were examined after 18 hours incubation to detect any change in morphology. The actin cytoskeleton was observed by immunofluorescence using fluorescent phalloidine isothyocyanate (1 µg/ml, Sigma) using the technique described by Giry et al. (Infect. Immun. 63 (1995) 4063-4071).

EXAMPLES

A—Cloning of the Complete Beta 2 Toxin of Type C *Clostridium perfringens*.

This example describes the cloning of the complete gene of the beta 2 toxin, i.e., including the regulation and addressing signals at the 5' end.

A 676 bp fragment essentially comprising the region coding for the mature form of the protein was isolated by amplification using the P279 and P280 deduced by microsequencing the protein (WO 95/17521). This fragment did not include the complete gene, in that no regulation signal was present at the 5' end of the gene. Further, the existence of addressing sequences was not revealed nor was it deducible from this fragment. With the aim of cloning the complete gene, the inventors firstly used this fragment as a probe to isolate, by hybridisation from a gene library, a fragment with a larger size comprising the 5' region. However, none of these experiments either detected or obtained a corresponding fragment, whatever the hybridisation conditions used. The inventors thus designed a different strategy to attempt to isolate a fragment carrying the 5' regions of the gene. In this regard, the inventors firstly circularised the matrix for amplification, then used inverse PCR on the DNA thus obtained using the P292 and P318 primers the sequence of which is as follows:

```
P318:
5'-GAAATGTTTACAACTGTATTAATATCGTAG-3'    (SEQ ID NO 4)

P292:
5'-TCAAGTTTGTACATGGGATGATG-3'           (SEQ ID NO 5)
```

The location of these primers on the gene is indicated in sequence SEQ ID no 1. The cloning strategy is shown in FIG.

1. The amplified fragment thus obtained was then sub-cloned in the pUC18 plasmid cleaved with SmaI, to generate the pMRP224 vector (FIG. 1).

The complete 1392 bp sequence of the fragment obtained is shown in sequence SEQ ID no 1.

B—Identification of Promoter Regions

The sequence obtained in Example A (SEQ ID no 1) comprises an open reading frame coding for the mature beta 2 toxin (residues 358 to 1122), and regulating or addressing regions located at the 5' and 3' end. The promoter region in the gene of the beta 2 toxin of type C *Clostridium perfringens* can be pinpointed on this sequence as comprising residues 1 to 267. This promoter sequence in the beta 2 toxin gene of type C *Clostridium perfringens* is shown separately in sequence SEQ ID no 3. This sequence includes a consensus ribosome binding site (GGGGGG) located 7 nucleotides upstream of the start codon ATG, i.e., at positions 255-260 in sequence SEQ ID no 3.

This region, or any fragment or variation thereof, can be isolated from samples of *Clostridium* nucleic acids using suitable probes (for example corresponding to sequence SEQ ID no 3 or a fragment thereof) or by chemical synthesis, or by enzymatic digestion from the plasmids of the invention, in particular the plasmid pMRP268, deposited on Aug. 8, 1997 at the Collection of the Institut Pasteur (CNCM: Collection Nationale de Cultures de Microorganismes), accession number I-1911.

This region, or any fragment or variation thereof, can be isolated from samples of *Clostridium* nucleic acids using suitable probes (for example corresponding to sequence SEQ ID no 2 or a fragment thereof) or by chemical synthesis, or by enzymatic digestion from the plasmids of the invention, in particular the plasmid pMRP268, deposited on Aug. 8, 1997 at the Collection of the Institut Pasteur 28, rue Docteur Roux; F-75724 Paris Cedex 15, France (CNCM: Collection Nationale de Cultures de Microorganismes), accession number I-1911.

The activity of the transcriptional promoter in this region or fragments or variants can be determined in different manners, in particular by inserting this region upstream of a reporter gene, and verifying the presence of the transcription or translation product of the reporter gene in a suitable cell host, in particular a bacterium from the genus *Clostridium*, more preferably *C. perfringens*.

The reporter gene can, for example, be the LacZ gene or the gene coding for luciferase.

The construction of these expression cassettes or vectors is shown in Examples D onwards, along with the transformation conditions for different cell hosts.

C—Identification of Addressing Regions

In addition to an open reading frame and transcription regulation regions (Example B), the sequence obtained in Example A (SEQ ID no 1) also comprises addressing signals enabling a protein or peptide to be directed during synthesis towards the host cell secretion routes. The addressing region (secretion signal peptide) of the beta 2 toxin gene of type C *Clostridium perfringens* can be seen in sequence SEQ ID no 1 as including residues 268 to 357. This signal peptide sequence of the beta 2 toxin gene of type C *Clostridium perfringens* is shown separately in sequence SEQ ID no 5. This region codes for 30 amino acids, comprising a hydrophobic region (residues 6-26), probably forming a transmembrane domain, bordered by charged amino acids (Lys2, Lys3, Lys7 and Lys27). Further, the junction region between this signal sequence and the mature protein (Ala30-Lys31) corresponds to the (Ala-X) cleavage site of the major portion of bacterial signal peptidases.

This region, or any fragment or variant thereof, can be isolated from samples of *Clostridium* nucleic acids using suitable probes (for example corresponding to sequence SEQ ID no 4 or a fragment thereof) or by chemical synthesis, or by enzymatic digestion from plasmids of the invention, in particular plasmid pMRP268, deposited on Aug. 8, 1997 in the Institut Pasteur collection (CNCM), accession number I-1911.

The signal sequence activity in this region or of fragments or variants can be checked in different manners, in particular by inserting this region upstream of a reporter gene, and verifying the presence of the translation product of this reporter gene in the culture supernatant of a suitable host cell, in particular a bacterium from the genus *Clostridium*, more preferably *C. perfringens*.

The construction of expression cassettes or vectors comprising this type of secretion signal is illustrated in the following examples which also give the transformation conditions in different cell hosts.

D—Construction of Expression Cassettes and Vectors

The regulation and addressing regions described in the invention can be inserted into any conventional expression vector, or used to construct expression cassettes.

These cassettes and vectors are particularly suitable for expression (and optionally secretion) of recombinant proteins in bacteria from the genus *Clostridium*, in particular *Clostridium perfringens*. It should be understood that any cell type in which these regions are functional can be used. These regions are particularly advantageous for expression of bacterial toxins, in particular toxins of bacteria from the genus *Clostridium*. The construction of suitable cassettes and vectors is described below.

Figure 2:
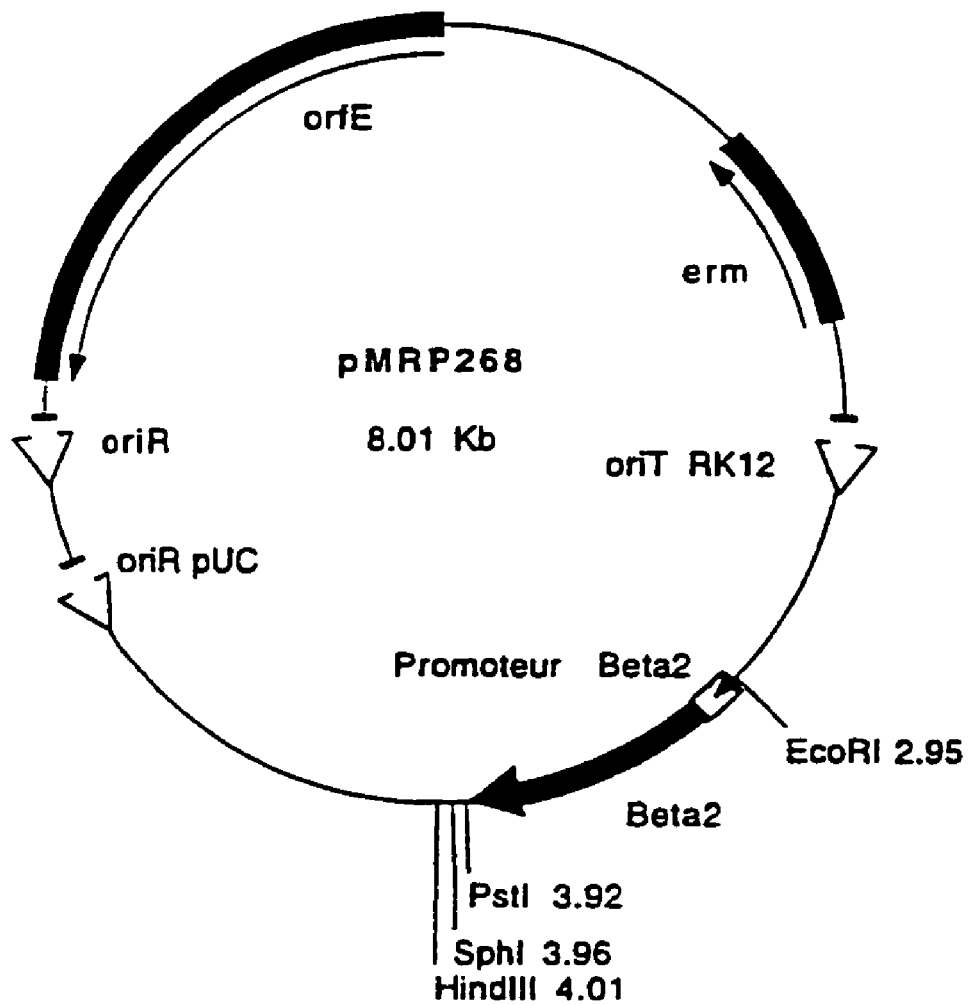
FIG. 2: Schematic representation of vector pMRP268.

D1. Construction of Vector pMRP268 (FIG. 2)

The vector pMRP268 carries the following elements:
an origin of replication OriR enabling its replication in an *E. coli* bacterium;
an origin of replication OriT enabling its replication in a bacterium from the genus *Clostridium*;
two marker genes (orfE and erm) enabling transformants in *E. coli* and *Clostridium* to be selected;
an expression cassette comprising, in the 5'→3' direction, the promoter for the beta 2 toxin of *Clostridium perfringens*, the secretion signal for the beta 2 toxin of *Clostridium perfringens*, and the sequence coding for the beta 2 toxin of *Clostridium perfringens*.

This vector was constructed from plasmid pAT19, by introducing the expression cassette into the cloning multi-site. More particularly, the cassette was obtained by amplification in the beta 2 gene of *Clostridium perfringens* of sequence SEQ ID no 1 using primers P385 and P393, the sequence and position of which are shown in SEQ ID no 1, using Vent Polymerase (Biolabs) following the recommendations of the manufacturer. The resulting amplification product was inserted into the EcoRl-PstI sites of plasmid pAT19. *C. perfringens* 667-76 strain not expressing lecithin and containing plasmid pMRP268 was deposited at the CNCM, Institut Pasteur, 28, rue Docteur Roux; F-75724 Paris Cedex 15, France on Aug. 8, 1997, accession number I-1911.

Figure 3:
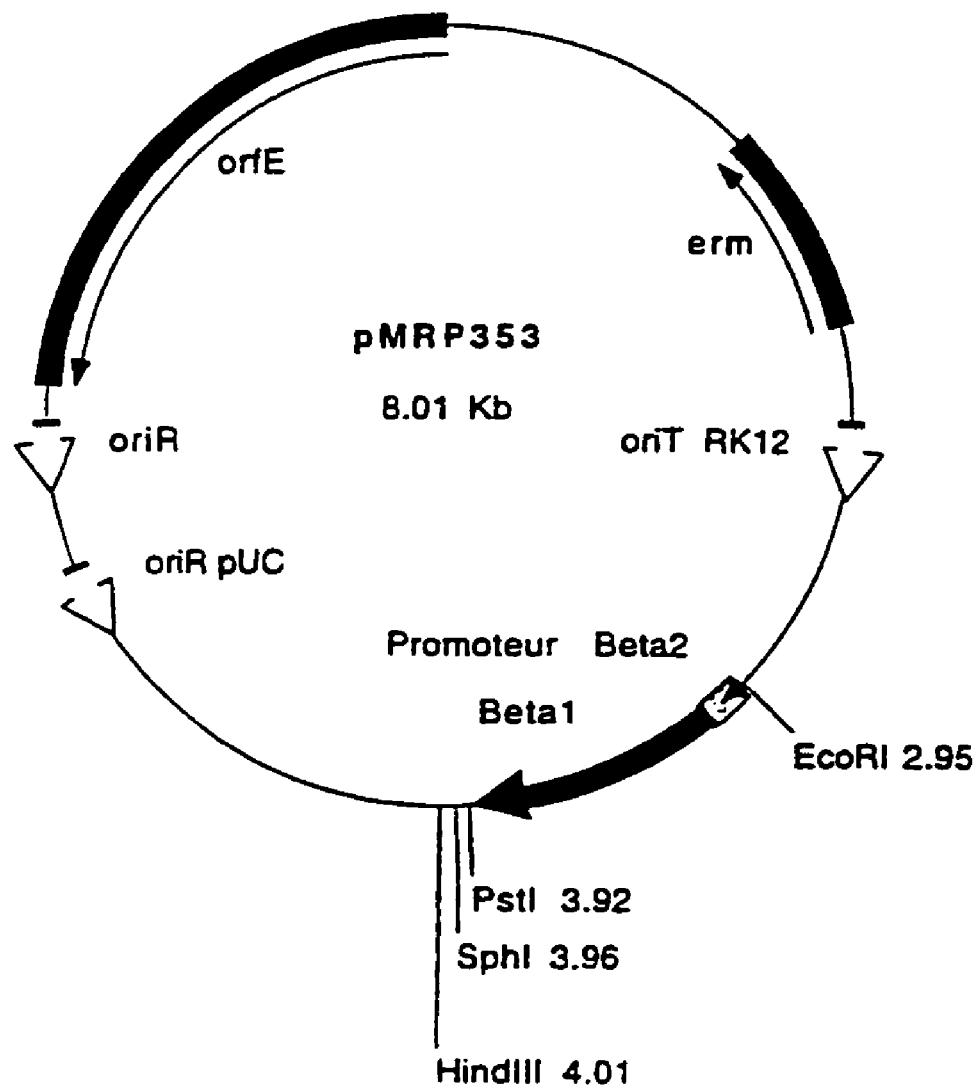
FIG. 3: Schematic representation of vector pMRP353.

D2. Construction of Vector pMRP353 (FIG. 3).

The vector pMRP353 carries the following elements:
an origin of replication OriR enabling its replication in an *E. coli* bacterium;
an origin of replication OriT enabling its replication in a bacterium from the genus *Clostridium*;
two marker genes (orfE and ern) enabling transformants in *E. coli* and *Clostridium* to be selected;

an expression cassette comprising, in the 5'→3' direction, the promoter for the beta 2 toxin of *Clostridium perfringens*, the secretion signal for the beta 2 toxin of *Clostridium perfringens*, and the sequence coding for the beta 1 toxin of *Clostridium perfringens*.

This vector was constructed from plasmid pMRP268 by substituting the sequence coding for the beta 2 toxin of *Clostridium pefringens* by that coding for the beta 1 toxin. The cDNA coding for the beta 1 toxin was obtained by amplification from strain NTCT8533 (Table 1) using primers introducing an NcoI site at the 5' end (P321) and a PstI site at the 3' end (P322).

D3. Construction of a Vector for Expression of any cDNA

It is clear that the vectors described in D1 and D2 above can be used to express any cDNA of interest under the control of a promoter region from the beta 2 gene, by substitution of the coding sequence, as illustrated in Example D2. Further, equivalent vectors can be constructed from other conventional plasmidic skeletons carrying other origins of replication and selection markers.

Figure 4:
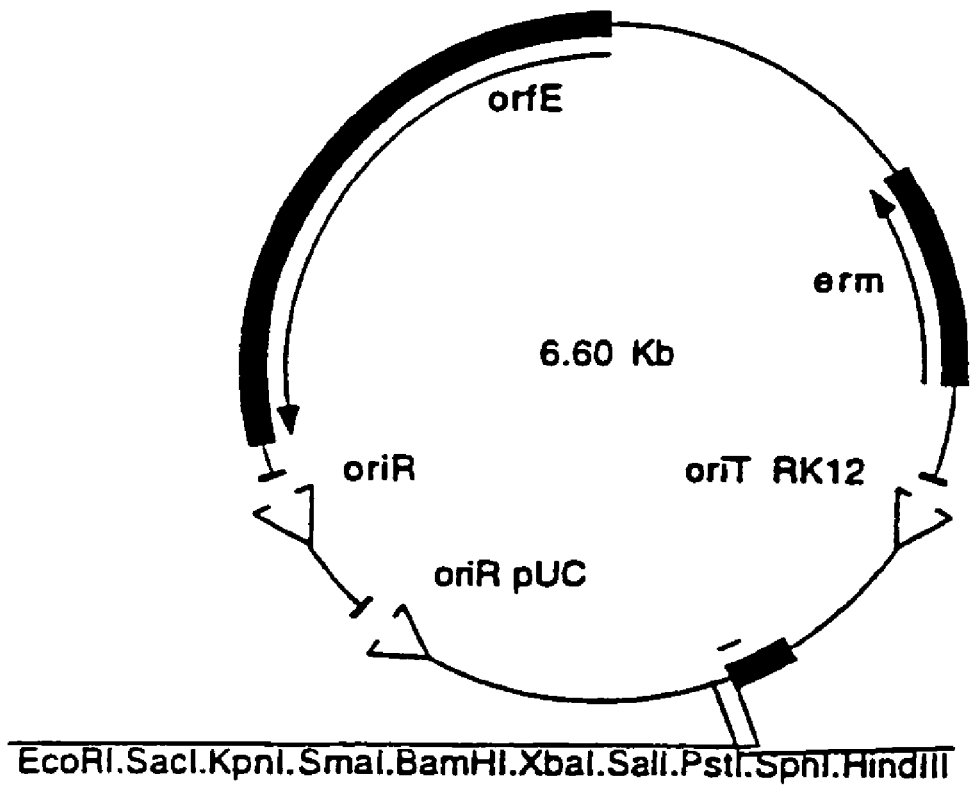
FIG. 4: Schematic representation of a plasmid carrying the beta 2 promoter.

FIG. 4 represents a vector carrying the promoter for the beta 2 gene of *Clostridium perfringens*, followed by a cloning multi-site enabling any cDNA of interest to be introduced.

E—Production and Purification of Recombinant Beta 2 Protein in *Clostridium*

Figure 5:
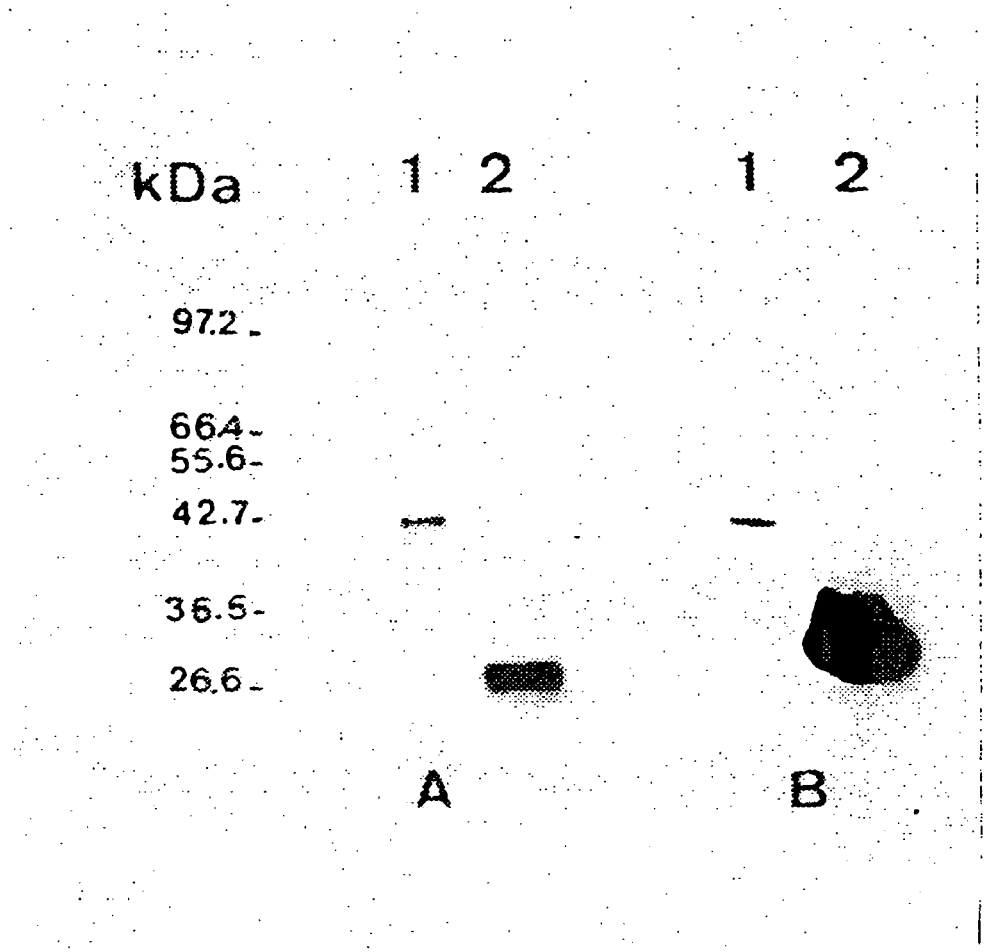
FIG. 5: SDS-PAGE and Western Blot analysis of purified recombinant beta 2 toxin: (A) SDS gel (0.1%)-PAGE (10%), stained with Coomassie blue for the beta 2 recombinant toxin (4.5 µg); (B) Corresponding Western Blot obtained with anti-beta 2 antibodies.

Plasmid pMRP268 was introduced into the *C. perfringens* 667-76 strain by electroporation (Perelle et al., 1993). The recombinant strain was cultivated overnight in a TGY medium containing 30 µg/ml of erythromycin, under anaerobic conditions at 37° C. The culture supernatant was then precipitated by saturation in the presence of 60% ammonium sulphate. The precipitate was dialysed against 10 mM Tris-HCl, pH 7.5, and charged onto a column of DEAE Sepharose CL6B. The column was then washed and eluted in the presence of 0.1 M NaCl in the same buffer. The eluted material was dialysed against 10 mM PIPES-HCl, pH 6.5, and charged onto a new column of DEAE Sepharose CL6B equilibrated with the same buffer. After washing, the column was eluted with a 0-0.1 M gradient of NaCl in a PIPES buffer. The fractions containing purified recombinant beta 2 toxin were concentrated. The apparent molecular weight of the recombinant protein, determined by SDS-PAGE, was 28 kDa, which agreed with the molecular weight calculated from the sequence (FIG. 5).

The results obtained thus show:
that it is possible to produce and secrete a recombinant toxin in *Clostridium* under the control of the beta 2 promoter;
that the recombinant toxin can be purified;
that the structure of the recombinant toxin does not appear to alter;
that the levels of expression obtained are higher by a factor of 10 than those observed in a wild strain of *Clostridium*.

One experiment was carried out under similar conditions, but introducing the expression vector not into the 667-76 strain (which does not produce the beta 2 toxin) but into a wild *Clostridium* strain. The results obtained show that the presence of the vectors of the invention in the *Clostridium* strains could increase the levels of production of the beta 2 toxin by a factor of 40 to 80.

These results demonstrate the advantages of the present invention. Thus the possibility of producing high levels of different types of toxins in a *Clostridium* strain can improve the immunogenic power of these supernatants, broaden the range of vaccines to encompass toxins which are naturally produced in only small amounts, and simplify the industrial production of vaccine compositions.

F—Production of the Recombinant Beta 1 Protein in *Clostridium*

Plasmid pMRP353 was introduced into the *C. perfringens* 667-76 strain by electroporation (Perelle et al., 1993). The recombinant strain was cultivated overnight in a TGY medium containing 30 µg/ml of erythromycin under anaerobic conditions at 37° C. The culture supernatant was treated as in Example E.

This experiment demonstrated the presence of recombinant beta 1 in the supernatants.

This example thus illustrates the capacity of the constructions of the invention to produce and secrete heterologous toxins (i.e., different from beta 2 or originating from pathogenic organisms other than *C. perfringens*) in *Clostridium* strains.

G—Production of Immunogenic Compositions

As indicated above, the present invention now enables before large quantities of different types of toxins to be produced in a strain of *Clostridium* which can form part of vaccine compositions. The invention thus improves the immunogenic power of these vaccines, broadens the range of vaccines to encompass toxins which are only naturally produced in small amounts, and simplifies the industrial production of vaccine compositions.

In particular, the present invention enables vaccines containing a toxoid of the beta 2 toxin to be produced, i.e., an inactivated form, to induce improved protection against infections by *Clostridium*. The advantages of such compositions are illustrated by the demonstration of important toxic properties of the beta 2 toxin.

G1. Properties of the Purified Recombinant Beta 2 Toxin

Figure 6:
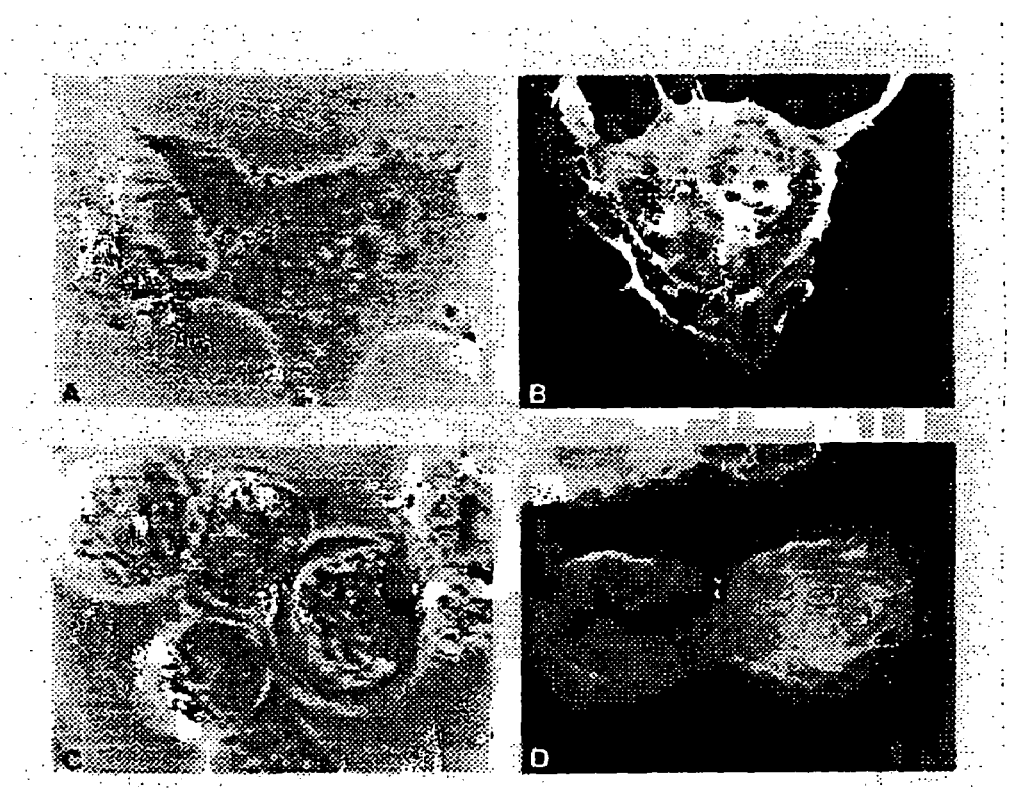
FIG. 6: Toxicity study of purified beta 2 toxin on I407 cells. Photos of I407 cells taken using a phase contrast microscope, control (A); treated with 20 µg/ml of beta 2 toxin for 18 hours (C). (B) and (D): view of actin cytoskeleton.

Purified beta 2 toxin was intravenously injected into mice. The results obtained showed that this toxin was lethal for mice in doses of less than 3 µg. Further, the results shown in FIG. 6 show that the beta 2 toxin was also toxic for I407 cells.

Figure 7:
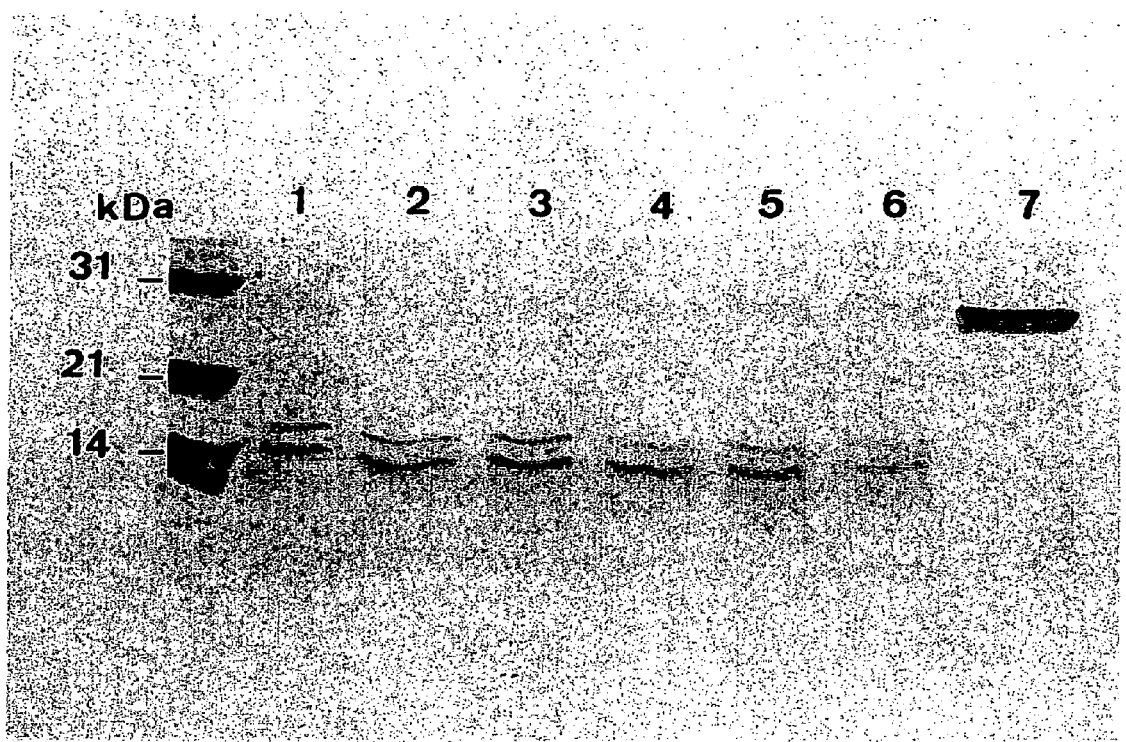
FIG. 7: Sensitivity of beta 2 toxin to trypsine. The beta 2 toxin (165 µg/ml) was incubated without (track 7) or with 16 ng/ml (track 1), 160 ng/ml (track 2), 400 ng/ml (track 3), 1.6 µg/ml (track 4), 4 µg/ml (track 5) and 16 µg/ml (track 6) of trypsin.
Figure 8A:
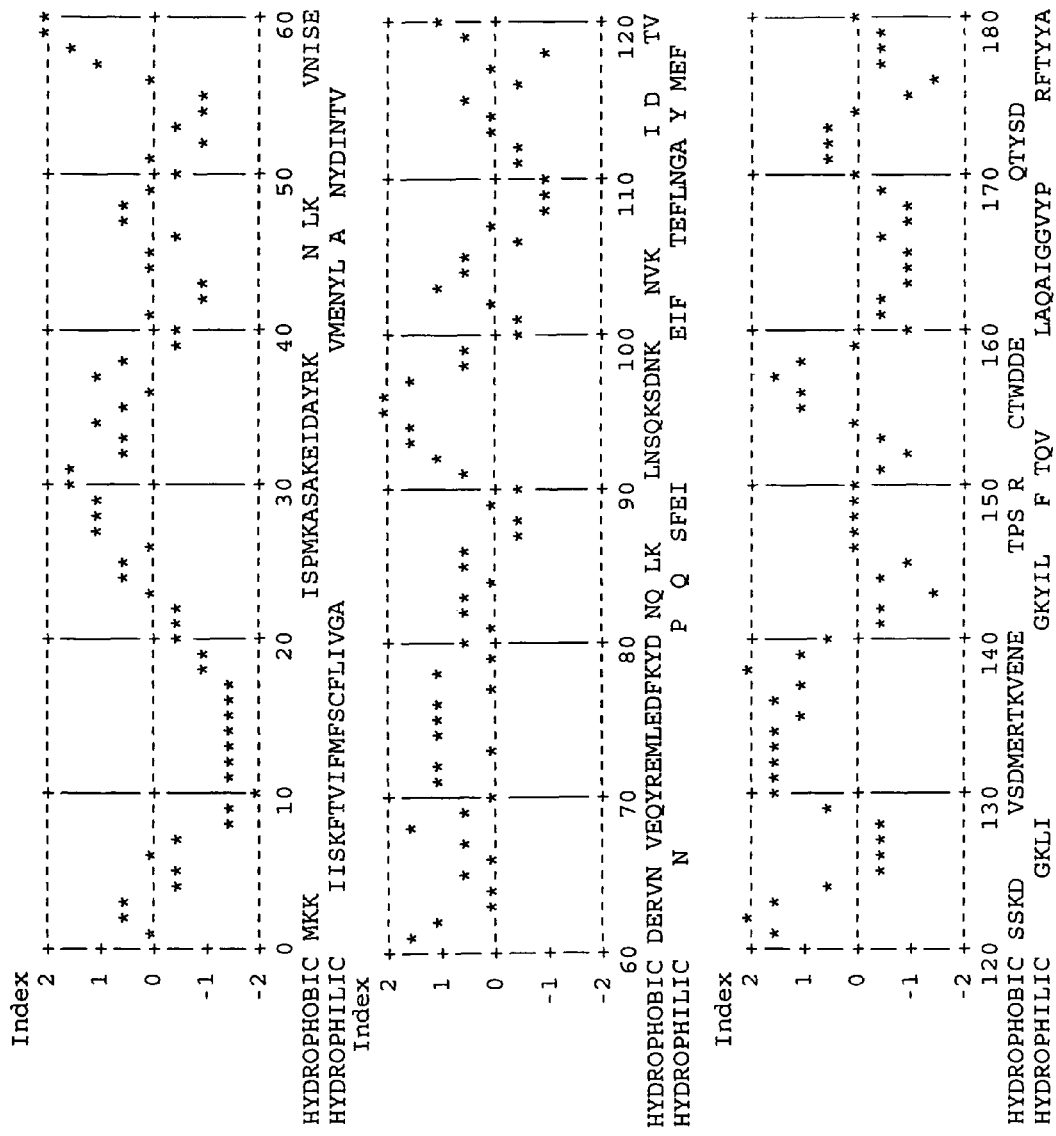
FIGS. 8A and 8B: Hydrophobicity profile for beta 2 toxin (SEQ ID NO: 2).
Figure 8B:
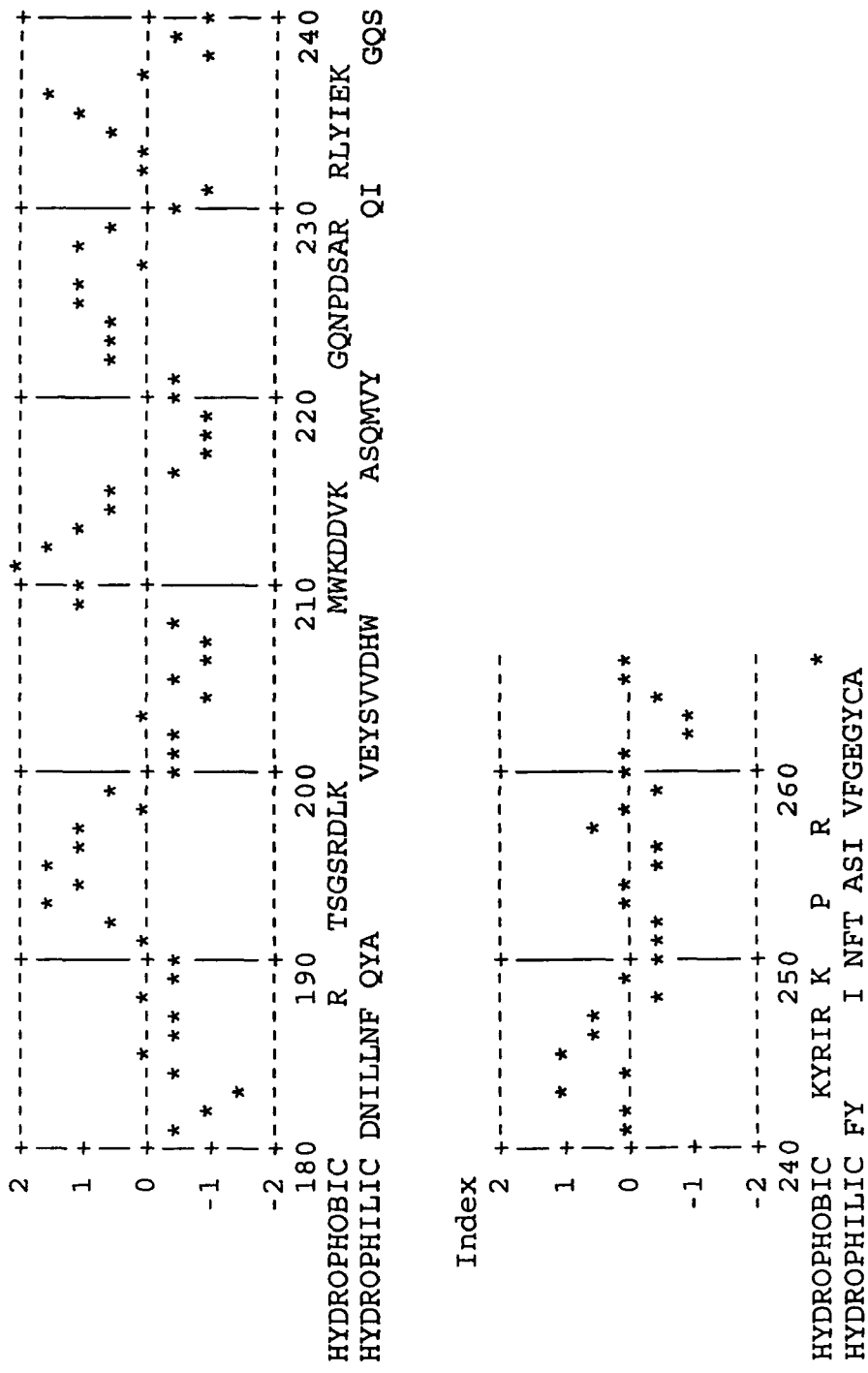

Further, the effect of treating beta 2 with trypsin on the activity of this toxin was evaluated. As shown in FIG. 7, 16 ng/ml of trypsin cleaved the beta 2 toxin into a 24 kDa constituent and at higher concentrations into two 13 and 15 kDa peptides. Cytotoxicity tests carried out with these trypsic digestion products showed a total absence of toxicity. Thus trypsin induces a loss of toxicity of the beta 2 toxin, and the peptides generated can be used as toxoids.

In order to determine the importance of the beta 2 toxin in the pathogenicity of *Clostridium*, the presence of the corresponding gene was analysed in 57 different strains of *Clostridium* (Tables 1 and 2). The results obtained shows that certain strains of type B and C *Clostridium* carry the beta 2 gene. In addition, of 27 strains isolated from young swine presenting with necrotic enteritis type lesions, 44% carried the beta 2 gene. Further, only the beta 2 gene was detected in all strains isolated from horses dying from colitis symptoms and in which *Clostridium perfringens* was harvested in large quantities (over $10^6$/g) from intestinal extracts. These results show the correlation between the beta 2 toxin and certain animal diseases, and the importance of being able to generate vaccine compositions wherein one of the antigens is a toxoid of the beta 2 toxin, in particular to vaccinate young swine and horses.

G2. Production of Immunogenic Compositions

This example illustrates the production of immunogenic compositions or vaccine compositions for protecting the organisms concerned against infections by pathogenic bacterial strains.

a) Polyvalent or Monovalent Compositions.

As indicated above, vaccine compositions can be monovalent (directed against a single toxin) or polyvalent (directed against a plurality of toxins). Commercially available toxins are generally polyvalent (Miloxan, Gletvax5). Preferred immunogenic compositions of the invention are also polyvalent. The immunogenic compositions of the invention advantageously comprise at least one recombinant toxoid produced in a recombinant cell of the invention. A further preferred immunogenic composition in the context of the invention advantageously comprises a toxoid of the beta 2 toxin of *C. perfringens*. The immunogenic compositions of the invention can also comprise any toxin mentioned above.

b) Production of an Immunogenic Composition Against the Beta 2 Toxin

In order to prepare such a composition, the culture supernatant from the *C. perfringens* strain transformed by the vector pMRP268 (Example E) was harvested using conventional techniques. This supernatant was centrifuged, then filtered and concentrated to obtain a preparation which was enriched in recombinant beta toxins. This preparation was then treated with formol to inactivate the toxins present. The treatment efficiency was determined by incubating I407 cells in the presence of a sample of this preparation.

This preparation was then used as an immunogen to induce the production of antibodies in an organism. The capacity of the antibodies produced to inhibit an infection by pathogenic strains of *Clostridium* could then be determined as described in the pharmacopia (*Vaccinum Clostridium perfringens*).

c) Production of a Polyvalent Immunogenic Composition

In order to prepare such a composition, the enriched composition obtained in Example b) above was mixed, before or after inactivation, with one or more other culture supernatants or derivative preparations comprising a toxin or the corresponding toxoid, such as a pertussis, cholera and/or tetanus toxoid. The resulting preparation was then checked and used as described in Example b).

TABLE 1

| Strains of type C *C. perfringens* | Presence of beta 2 toxin gene |
|---|---|
| NCTC8533 | − |
| NCTC6121 | − |
| ATCC3628 | − |
| NCTC8081 | − |
| NCTC3180 | + |
| NCTC3182 | + |

TABLE 2

| | | Presence of genes | | |
|---|---|---|---|---|
| Isolates from | Total *Clostridium* | cpb2+, cpb1− | cpb2+, cpb1+ | cpb2−, cpb1− |
| Young swine | 27 | 12 | 12 | 1 |
| Horses | 15 | 16 | 0 | 0 |
| Foodstuffs | 15 | 2 | 0 | 0 | cpb2: gene of beta 2 toxin;
cpb1: gene of beta 1 toxin

The invention claimed is:

1. An immunogenic composition, comprising an isolated beta 2 precursor toxin encoded by plasmid pMRP268 deposited at the CNCM on Aug. 8, 1997 under accession number I-1911.

* * * * *

SEQUENCE LISTING

```
<160> NUMBER OF SEQ ID NOS: 8

<210> SEQ ID NO 1
<211> LENGTH: 1392
<212> TYPE: DNA
<213> ORGANISM: Clostridium perfringens
<220> FEATURE:
<221> NAME/KEY: CDS
<222> LOCATION: (268)..(1065)

<400> SEQUENCE: 1
atttgggata tcttaaattt agcacagaag aatgtttaaa tgaaataaag ataataaaaa        60
gatatattaa ttatatagct gaaaatttat aattatatga taagtatagt taataaataa       120
aaagtgttct cgggggacac ttttttgttt taaaaaggaa aatataaata aaatttagat       180
aaaagtgtaa aataattatt tttatttaa atttgttaaa aatttgatat aattgaattg        240
taaaaaaaat ttcagggggg aatataa atg aaa aaa att att tca aag ttt act       294
                                Met Lys Lys Ile Ile Ser Lys Phe Thr
                                  1               5 gta att ttt atg ttt tca tgt ttt ctt att gtt gga gca ata agt cca       342
Val Ile Phe Met Phe Ser Cys Phe Leu Ile Val Gly Ala Ile Ser Pro
 10              15                  20                  25 atg aaa gca agt gca aaa gaa atc gac gct tat aga aag gta atg gag       390
Met Lys Ala Ser Ala Lys Glu Ile Asp Ala Tyr Arg Lys Val Met Glu
                 30                  35                  40 aat tat ctt aat gct tta aaa aac tac gat att aat aca gtt gta aac       438
Asn Tyr Leu Asn Ala Leu Lys Asn Tyr Asp Ile Asn Thr Val Val Asn
             45                  50                  55 att tca gaa gat gaa aga gta aat aat gtt gaa cag tat aga gaa atg       486
Ile Ser Glu Asp Glu Arg Val Asn Asn Val Glu Gln Tyr Arg Glu Met
         60                  65                  70
```

```
tta gaa gat ttt aaa tat gat cct aac caa caa ctg aaa tct ttt gaa   534
Leu Glu Asp Phe Lys Tyr Asp Pro Asn Gln Gln Leu Lys Ser Phe Glu
    75                  80                  85 ata ctt aat tca caa aag agc gat aat aaa gaa ata ttt aat gta aaa   582
Ile Leu Asn Ser Gln Lys Ser Asp Asn Lys Glu Ile Phe Asn Val Lys
 90                  95                 100                 105 act gaa ttt tta aat ggt gca att tat gat atg gaa ttt act gta tca   630
Thr Glu Phe Leu Asn Gly Ala Ile Tyr Asp Met Glu Phe Thr Val Ser
                110                 115                 120 tct aaa gat gga aaa tta ata gta tct gat atg gaa aga aca aaa gtt   678
Ser Lys Asp Gly Lys Leu Ile Val Ser Asp Met Glu Arg Thr Lys Val
            125                 130                 135 gag aat gaa gga aaa tat att tta aca cca tca ttt aga act caa gtt   726
Glu Asn Glu Gly Lys Tyr Ile Leu Thr Pro Ser Phe Arg Thr Gln Val
        140                 145                 150 tgt aca tgg gat gat gaa cta gca caa gca att ggg gga gtt tat cca   774
Cys Thr Trp Asp Asp Glu Leu Ala Gln Ala Ile Gly Gly Val Tyr Pro
    155                 160                 165 caa aca tat tct gat aga ttt aca tat tat gca gat aat ata tta tta   822
Gln Thr Tyr Ser Asp Arg Phe Thr Tyr Tyr Ala Asp Asn Ile Leu Leu
170                 175                 180                 185 aac ttc aga caa tat gca act tca ggt tca aga gat tta aaa gta gaa   870
Asn Phe Arg Gln Tyr Ala Thr Ser Gly Ser Arg Asp Leu Lys Val Glu
                190                 195                 200 tat agt gtt gta gat cat tgg atg tgg aaa gat gat gtt aaa gct tct   918
Tyr Ser Val Val Asp His Trp Met Trp Lys Asp Asp Val Lys Ala Ser
            205                 210                 215 caa atg gta tat ggt caa aat cct gat tct gct aga caa ata aga tta   966
Gln Met Val Tyr Gly Gln Asn Pro Asp Ser Ala Arg Gln Ile Arg Leu
        220                 225                 230 tat ata gaa aaa gga caa tct ttc tat aaa tat aga ata aga att aaa  1014
Tyr Ile Glu Lys Gly Gln Ser Phe Tyr Lys Tyr Arg Ile Arg Ile Lys
    235                 240                 245 aac ttt aca cct gca tca att aga gta ttt ggt gaa ggg tat tgt gca  1062
Asn Phe Thr Pro Ala Ser Ile Arg Val Phe Gly Glu Gly Tyr Cys Ala
250                 255                 260                 265 tag aaaaaaatat gaagtgactt agtcacttca tattttttt actattaatt       1115 ttattatata aaaacctaac atacatgaaa gtattcttaa tacagttata tcaaaattaa 1175 agtaggggaa ataaaataaa aggctaaaaa ctatattaaa aactataaaa attattaaat 1235 taggttttaa ggtgttatat ttatttatga ttataggaat aaatatgcca aatggaataa 1295 ataaagtaa tattaataat tggtctaaaa agtatacatc attgataaaa gaaaaattac 1355 cagtaaaaat tgagcttaaa aaattaaatg taaattt                        1392

<210> SEQ ID NO 2
<211> LENGTH: 265
<212> TYPE: PRT
<213> ORGANISM: Clostridium perfringens

<400> SEQUENCE: 2

Met Lys Lys Ile Ile Ser Lys Phe Thr Val Ile Phe Met Phe Ser Cys
1               5                   10                  15

Phe Leu Ile Val Gly Ala Ile Ser Pro Met Lys Ala Ser Ala Lys Glu
            20                  25                  30

Ile Asp Ala Tyr Arg Lys Val Met Glu Asn Tyr Leu Asn Ala Leu Lys
        35                  40                  45

Asn Tyr Asp Ile Asn Thr Val Val Asn Ile Ser Glu Asp Glu Arg Val
    50                  55                  60
```

```
Asn Asn Val Glu Gln Tyr Arg Glu Met Leu Glu Asp Phe Lys Tyr Asp
 65                  70                  75                  80

Pro Asn Gln Gln Leu Lys Ser Phe Glu Ile Leu Asn Ser Gln Lys Ser
                 85                  90                  95

Asp Asn Lys Glu Ile Phe Asn Val Lys Thr Glu Phe Leu Asn Gly Ala
            100                 105                 110

Ile Tyr Asp Met Glu Phe Thr Val Ser Ser Lys Asp Gly Lys Leu Ile
            115                 120                 125

Val Ser Asp Met Glu Arg Thr Lys Val Glu Asn Glu Gly Lys Tyr Ile
130                 135                 140

Leu Thr Pro Ser Phe Arg Thr Gln Val Cys Thr Trp Asp Asp Glu Leu
145                 150                 155                 160

Ala Gln Ala Ile Gly Gly Val Tyr Pro Gln Thr Tyr Ser Asp Arg Phe
                165                 170                 175

Thr Tyr Tyr Ala Asp Asn Ile Leu Leu Asn Phe Arg Gln Tyr Ala Thr
            180                 185                 190

Ser Gly Ser Arg Asp Leu Lys Val Glu Tyr Ser Val Val Asp His Trp
            195                 200                 205

Met Trp Lys Asp Val Lys Ala Ser Gln Met Val Tyr Gly Gln Asn
            210                 215                 220

Pro Asp Ser Ala Arg Gln Ile Arg Leu Tyr Ile Glu Lys Gly Gln Ser
225                 230                 235                 240

Phe Tyr Lys Tyr Arg Ile Arg Ile Lys Asn Phe Thr Pro Ala Ser Ile
                245                 250                 255

Arg Val Phe Gly Glu Gly Tyr Cys Ala
            260                 265

<210> SEQ ID NO 3
<211> LENGTH: 267
<212> TYPE: DNA
<213> ORGANISM: Clostridium perfringens

<400> SEQUENCE: 3
atttgggata tcttaaattt agcacagaag aatgtttaaa tgaaataaag ataataaaaa      60
gatatattaa ttatatagct gaaaatttat aattatatga taagtatagt taataaataa     120
aaagtgttct cggggacac ttttttgttt taaaaaggaa aatataaata aaatttagat      180 aaagtgtaa ataattatt tttattttaa atttgttaaa aatttgatat aattgaattg       240
taaaaaaaat ttcagggggg aatataa                                         267

<210> SEQ ID NO 4
<211> LENGTH: 90
<212> TYPE: DNA
<213> ORGANISM: Clostridium perfringens
<220> FEATURE:
<221> NAME/KEY: CDS
<222> LOCATION: (1)..(90)

<400> SEQUENCE: 4 atg aaa aaa att att tca aag ttt act gta att ttt atg ttt tca tgt      48
Met Lys Lys Ile Ile Ser Lys Phe Thr Val Ile Phe Met Phe Ser Cys
  1               5                  10                  15 ttt ctt att gtt gga gca ata agt cca atg aaa gca agt gca              90
Phe Leu Ile Val Gly Ala Ile Ser Pro Met Lys Ala Ser Ala
                 20                  25                  30

<210> SEQ ID NO 5
<211> LENGTH: 30
<212> TYPE: PRT
```

-continued

```
<213> ORGANISM: Clostridium perfringens

<400> SEQUENCE: 5

Met Lys Lys Ile Ile Ser Lys Phe Thr Val Ile Phe Met Phe Ser Cys
1               5                   10                  15

Phe Leu Ile Val Gly Ala Ile Ser Pro Met Lys Ala Ser Ala
            20                  25                  30

<210> SEQ ID NO 6
<211> LENGTH: 30
<212> TYPE: DNA
<213> ORGANISM: Artificial Sequence
<220> FEATURE:
<223> OTHER INFORMATION: synthetic DNA

<400> SEQUENCE: 6
gaaatgttta caactgtatt aatatcgtag                                        30

<210> SEQ ID NO 7
<211> LENGTH: 23
<212> TYPE: DNA
<213> ORGANISM: Artificial Sequence
<220> FEATURE:
<223> OTHER INFORMATION: synthetic DNA

<400> SEQUENCE: 7
tcaagtttgt acatgggatg atg                                               23

<210> SEQ ID NO 8
<211> LENGTH: 327
<212> TYPE: DNA
<213> ORGANISM: Clostridium perfringens

<400> SEQUENCE: 8
atttgggata tcttaaattt agcacagaag aatgtttaaa tgaaataaag ataataaaaa       60
gatatattaa ttatatagct gaaaatttat aattatatga taagtatagt taataaataa      120
aaagtgttct cgggggacac ttttttgttt taaaaaggaa aatataaata aaatttagat      180
aaaagtgtaa aataattatt tttattttaa atttgttaaa aatttgatat aattgaattg      240
taaaaaaaat ttcagggggg aatataaatg aaaaaaatta tttcaaagtt tactgtaatt      300
tttatgtttt catgttttct tattgtt                                         327
```